United States Patent
Boyle et al.

(10) Patent No.: US 11,666,422 B2
(45) Date of Patent: Jun. 6, 2023

(54) CBCT IMAGING OF IMPRESSION HAVING IMPLANT LOCATOR

(71) Applicant: TROPHY, Croissy Beaubourg (FR)

(72) Inventors: Eamonn Boyle, Croissy Beaubourg (FR); Marianne Belcari, Croissy Beaubourg (FR); Xavier Ripoche, Mandres les Roses (FR)

( * ) Notice: Subject to any disclaimer, the term of this patent is extended or adjusted under 35 U.S.C. 154(b) by 735 days.

(21) Appl. No.: 16/610,621

(22) PCT Filed: May 4, 2017

(86) PCT No.: PCT/IB2017/000758
§ 371 (c)(1),
(2) Date: Nov. 4, 2019

(87) PCT Pub. No.: WO2018/203102
PCT Pub. Date: Nov. 8, 2018

(65) Prior Publication Data
US 2020/0060793 A1 Feb. 27, 2020

(51) Int. Cl.
| | | |
|---|---|---|
| *G06K 9/00* | (2022.01) |
| *A61C 13/00* | (2006.01) |
| *A61C 8/00* | (2006.01) |
| *A61C 9/00* | (2006.01) |
| *A61B 6/14* | (2006.01) |
| *G06T 11/00* | (2006.01) |
| *A61B 6/03* | (2006.01) |

(52) U.S. Cl.
CPC .......... *A61C 13/0004* (2013.01); *A61B 6/14* (2013.01); *A61C 8/0001* (2013.01); *A61C 9/0006* (2013.01); *A61C 9/0046* (2013.01); *G06T 11/003* (2013.01); *A61B 6/032* (2013.01); *G06T 2211/40* (2013.01); *G06T 2211/416* (2013.01)

(58) Field of Classification Search
CPC . A61C 13/0004; A61C 8/0001; A61C 9/0006; A61C 9/0046; G06T 11/003; G06T 2211/40; G06T 2211/416
See application file for complete search history.

(56) References Cited

U.S. PATENT DOCUMENTS

2009/0113714 A1* 5/2009 Greenberg ............... B21F 43/00
29/896.11
2010/0184002 A1* 7/2010 Ranck .................. A61C 8/0001
433/172

(Continued)

*Primary Examiner* — Avinash Yentrapati

(57) ABSTRACT

Embodiments provide the capability to determine a digital 3D model of a patient's teeth obtains projection images acquired by scanning a negative impression of the patient's teeth using a computed tomographic imaging apparatus, where the impression includes a radio-opaque transfer element for a dental implant or crown post. One exemplary method reconstructs, from the projection images, an air volume model within the reconstructed volume and bounded by a transition surface defined according to the negative impression. A transfer element volume model of the transfer element is defined, segmented from the air volume model and from the transition surface. A combined digital 3D model of the patient's teeth is formed according to the air volume model and transfer element volume model. At least a portion of the combined digital 3D model of the teeth is displayed.

20 Claims, 9 Drawing Sheets

(56) References Cited

U.S. PATENT DOCUMENTS

2014/0120488 A1* 5/2014 Greenberg ............. A61C 7/002
433/6
2016/0148370 A1* 5/2016 Maury .................. G06T 7/0012
348/77

* cited by examiner

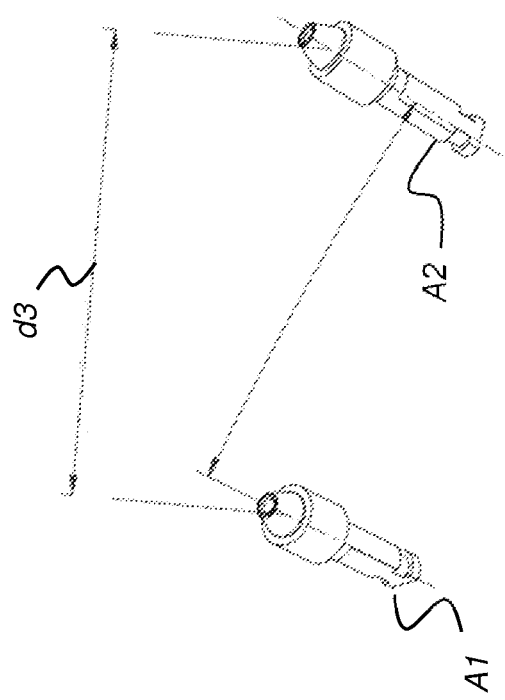

US 11,666,422 B2

CBCT IMAGING OF IMPRESSION HAVING IMPLANT LOCATOR

TECHNICAL FIELD

The present invention is related generally to dental imaging and more particularly to methods and/or apparatus for forming digital volume images for dental modeling and restoration.

BACKGROUND OF THE INVENTION

Dental study casts are widely used in general dentistry and related disciplines and help to provide improved understanding of how a patient's teeth and bite function. The study of the static relationship of teeth and bite that is provided serves a number of functions, including a diagnostic function for interpretation of discrepancies or problems related to the bite relationship. The study casts that are formed further improve communication as a concrete, physical model, helping the practitioner and patient to better understand discrepancies in tooth function and restorative treatment. The dental study cast also helps to more precisely define pre-existing static bite relationships prior to the performance of any corrective work.

The plaster cast is formed using a series of impressions taken to obtain the geometry of the teeth. To take an impression, alginate or other impression material is poured into a tray (i.e., an impression tray) which is then introduced into the patient's mouth for a period of time (typically one to two minutes). The impression material sets about the teeth and soft tissues, forming a negative impression. The patient also bites into a soft material for registering a simultaneous imprint of the upper and lower teeth which records the relationship of the teeth in the upper and lower jaws respectively, in three planes of space. Once the impressions have set, they are sent to a lab to be processed into an upper and/or lower plaster study cast, also termed a dental stone cast. The study casts for upper and lower jaws can be articulated together via the bite registration material to model the bite of the patient. After construction, the study casts are returned to the dental practitioner as a working study cast.

Drawbacks of conventional preparation methods relate to the number of labor-intensive steps required to produce the study casts, the space and storage requirements of the study casts, and the inability to interface the study casts interactively with other diagnosis information (e.g., photographs and radiographs). Due to the multiple manual stages, errors and tolerance problems can tend to propagate from one step to the next. In some cases, if additional work is required, or if the cast fails in some way or is damaged or lost, an additional impression series must be taken. Therefore, there also exists a need in the art to develop a set of electronic data from the series of dental impressions wherein only a single impression need be taken for multiple interactive functions.

In a conventional sequence for orthodontic or restorative planning, the plaster cast that represents the patient's teeth can then be scanned, such as using laser scanning or using a computed tomography (CT) or a cone-beam computed tomography (CBCT) scanning apparatus. The scanned data then provides baseline information for forming a digital model of the patient's dentition. The digital model that is formed can be used for a range of functions, including implant planning and design, crown design and positioning, orthodontic guidance, and other complex tasks that benefit from 3D (three-dimensional) modeling. Use of a digital model allows visibility of a treatment area from any desired perspective and can help to provide more accurate data on measurement, shape, and orientation of intraoral features.

For conventional approaches to providing a model of teeth in the upper and/or lower jaw of a patient, reference is made to Patent Application number WO2008US75658 by Puttler et al.; published Apr. 2, 2009, and to U.S. Pat. No. 8,573,972 to Matov et al issued Nov. 5, 2013. Reference is also made to U.S. Pat. Nos. 7,140,877 and 6,767,208 to Kaza. Scanning of the mouth or an impression using optical systems is described, for example, in U.S. Pat. No. 7,905,725 to Chisti et al. Scanning of the mouth in vivo or of an impression using a hand-held scanning device is described in U.S. Pat. No. 7,068,825 to Rubbert et al. Laser scanning of teeth or impressions is described in U.S. Pat. No. 6,217,334 to Hultgren.

There are some applications where conventional scanning techniques used to obtain image content from a stone or plaster model are particularly disadvantaged. These include implant supported crowns and post-and-core restorations, which form the basis for the final dental crown prosthetics. For these applications, as well as for a broad range of orthodontic and other dental functions, the extra step of forming the stone or plaster cast adds cost and delay to the dental imaging process as well as risking potential loss of precision and information. Transfer and mounting apparatus temporarily or permanently installed can be difficult to accurately characterize using conventional scan methods. Moreover, transporting and handling of the dental impression must be done with care, as the impression materials are soft and can easily be distorted in transit.

Thus, it can be appreciated that there would be advantages to exemplary apparatus and method embodiments that can reduce or eliminate workflow steps and reduce the time and/or labor needed to provide intraoral impression data in digital form.

SUMMARY

Embodiments of the present disclosure address the need for improved methods for generating a 3D model of intraoral surfaces and features. The present disclosure provides exemplary method and/or apparatus embodiments to create a digital model of a patient's teeth, using an impression of the patient's teeth and scanning the impression using an X-ray source to generate the digital model, where the model can also show position and orientation of features used for implant, crown, orthodontic, and/or other treatments.

Advantages of the disclosure may include eliminating the requirement to fabricate plaster models of a patient's dentition in many cases, including cases requiring implant and crown prosthetics. The capability for digital manipulation, detailing, and image correction helps to improve overall accuracy of results, without the added complexity, materials, and labor required for a stone or plaster model.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a method comprising:
    obtaining a plurality of projection images acquired by scanning a negative impression of the patient's teeth using a computed tomographic imaging apparatus, wherein the impression includes a radio-opaque transfer element for a dental implant or crown post;

forming a reconstructed volume from the plurality of projection images; defining an air volume model within the reconstructed volume and bounded by a transition surface defined according to the negative impression;

defining a transfer element volume model of the transfer element, segmented from the air volume model and from the transition surface;

forming a combined digital 3D model of the patient's teeth according to the air volume model and transfer element volume model;

and displaying at least a portion of the combined digital 3D model of the teeth.

BRIEF DESCRIPTION OF THE DRAWINGS

The foregoing and other objects, features, and advantages of the invention will be apparent from the following more particular description of exemplary embodiments of the invention, as illustrated in the accompanying drawings. The elements of the drawings are not necessarily to scale relative to each other.

FIGS. 6A, 6B, and 6C show different views of transfer elements from different plane perspectives.

DESCRIPTION OF EXEMPLARY EMBODIMENTS

Figure 1:
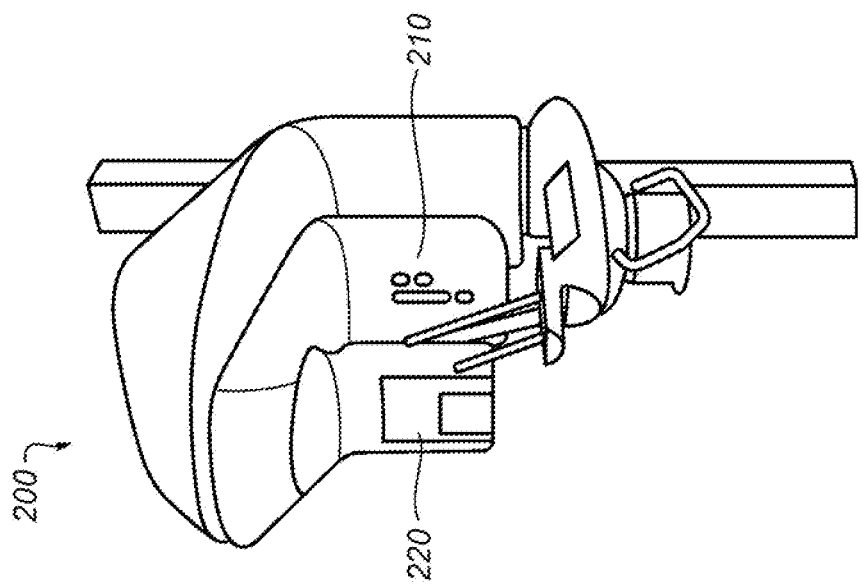
FIG. 1 shows a perspective view of a CT scanner.

The following is a description of exemplary method and/or apparatus embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

In the context of the present disclosure, the term "volume image" is synonymous with the terms "3-Dimensional image" or "3-D image". An image slice or "2-D slice" is a 2-D image that has been extracted from the full 3-D volume.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D projection images of pixels, taken at different relative angles, then combining the projection image data to form corresponding 3-D voxels. For the purposes of the description herein, the terms voxel and pixel can generally be considered equivalent, describing an image elemental datum that is capable of having a range of numerical values. Voxels and pixels have the attributes of both spatial location and image data code value.

In the context of the present disclosure, the terms "viewer", "operator", "viewing practitioner", "observer", and "user" are considered to be equivalent and refer to the viewing practitioner or other person who views and manipulates a radiographic image on a display monitor or other viewing apparatus. Viewer preferences relate to the particular viewer who observes a displayed image or image slice.

As used herein, the term "energizable" relates to a device or set of components that perform an indicated function upon receiving power and, optionally, upon receiving an enabling signal.

CT and CBCT imaging utilize 2-D radiographic data in order to form a 3-D image volume. In this type of imaging, the same voxel (that is, the same point in space) is measured multiple times. For example, a first radiation beam is directed through the voxel at a first angle and a portion of this radiation, proportional to the density of the material, passes through the voxel and forms an image on the detector. This process then repeats at a second angle, a third angle, and so on. The capability to obtain radiodensity information of a voxel from multiple angles allows information about the material content of the voxel to be deduced. An attenuation coefficient $\mu$ can be determined or approximated for the voxel, in terms of CT numbers, in terms of relative or actual Hounsfield units, or on some other appropriate scale. The attenuation coefficient or corresponding attenuation data can then be used to yield information about the type of tissue or composition of material that is being measured. The applicants have developed techniques for developing and refining relative attenuation information for voxels from the CT or CBCT scan data and for using this information for obtaining accurate information related to the tooth surfaces, without requiring a direct scan of the patient anatomy and without requiring that a plaster cast be formed from an impression obtained from the patient's mouth.

Reference is hereby made to commonly assigned U.S. Patent Application No. 2016/1048370 by Maury, et al., incorporated herein by reference in its entirety.

Conventional practice for designing and planning a dental implant or crown restoration requires a sequence of steps that generally follow this pattern:

(i) prepare the restoration or implant site to include a support feature and a locator element;

(ii) obtain an impression of the patient's dentition using an appropriate impression material;

(iii) position the locator element in the obtained impression;

(iv) form a positive model of the patient's dentition and locator using the impression as a mold;

(v) use the locator to digitally position an analogue of the implant in the stone or impression;

(vi) design the restoration using the positive model.

Certain exemplary method and/or apparatus embodiments of the present disclosure can provide a digital model of patient dentition that includes one or more locator element for an implant, crown, or other restoration, wherein the digital model is obtained by scanning the impression along with its locator element. Exemplary method and/or apparatus embodiments can be used for dental implant planning, or as part of post-and-core workflow, or for any other type of dental restoration that has some portion of supporting hardware structure inserted into the patient's jaw. In exemplary embodiments described herein, the step of forming a positive model (iv) is eliminated, with scanning of the impression and locator element forming a digital model of the appropriate dentition.

As described in the Maury et al. reference, a CBCT (cone beam computed tomography) scanner is one type of scanning system that can be employed to scan an impression model (either a positive impression or a negative impression) of the patient's teeth. FIG. 1 shows an example of a CT scanner 200 used for dental imaging. CT scanner 200 has an x-ray source 210 and a detector 220 that orbit the patient for obtaining multiple 2-D projection images that are used to generate a volume image. In a preferred arrangement, a CBCT system is used. CT scanner 200 can perform trajectories including an axis of rotation that is fixed or movable in one direction or movable in a plane or two directions.

Figure 2:
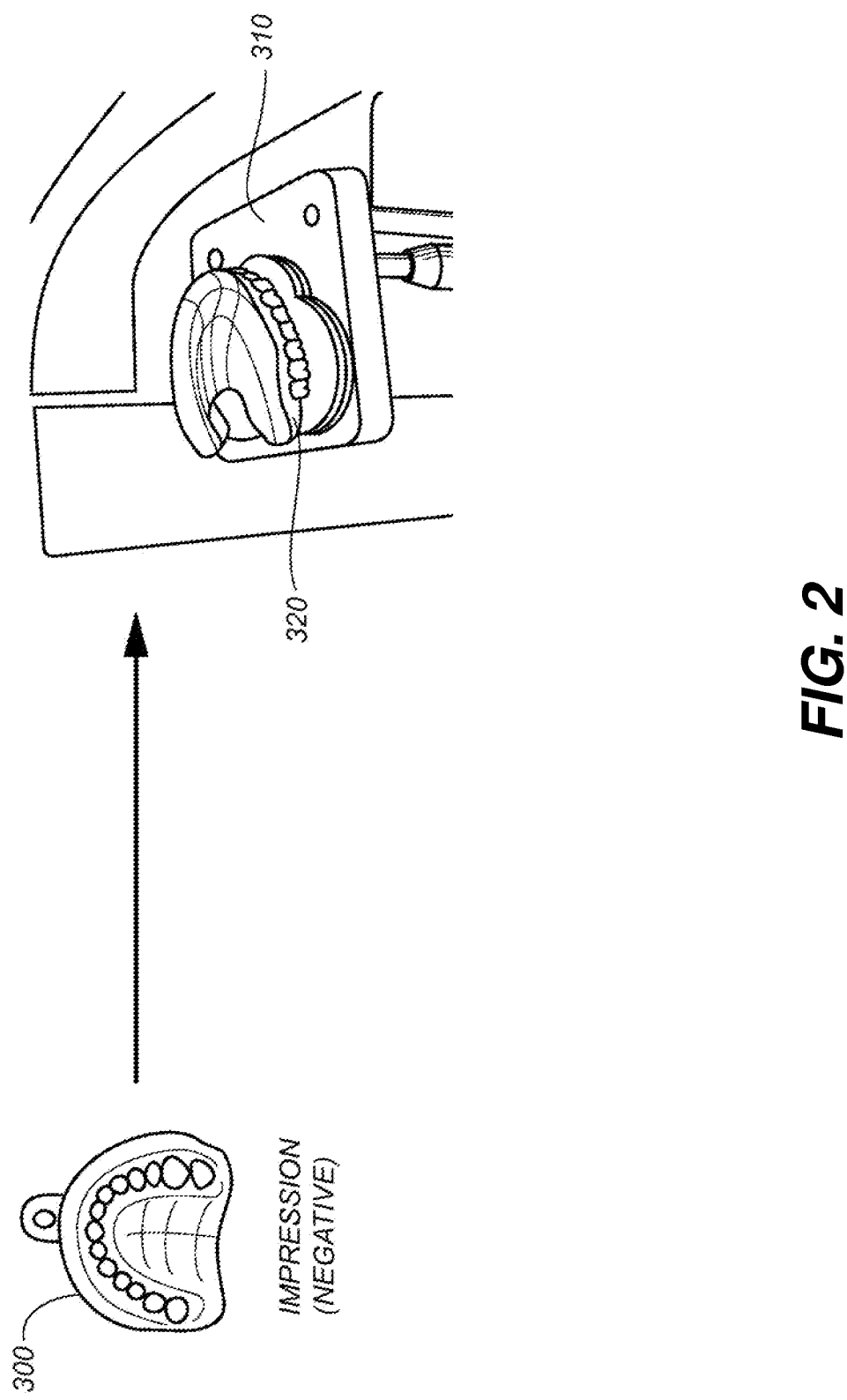
FIG. 2 shows an impression for forming a plaster model that can be scanned using CT scanner.

FIG. 2 shows use of an impression 300 for forming a stone or plaster model 320 that can be scanned using CT scanner 200. The scanner can be an x-ray scanner. An example of an x-ray scanner is a Computed Tomography (CT) system, which utilizes fan-beam CT or cone-beam CT (CBCT) techniques, well-known in the diagnostic imaging arts. Embodiments of the present disclosure can scan impression 300 directly for obtaining a digital model of the patient's teeth. Alternately, CT scanner 200 can be used to scan stone or plaster model 320 or both impression 300 and plaster model 320. Optionally, a bite registration material can be scanned.

The impression is typically obtained from a dental practitioner and can be any suitable impression material, such as polyvinyl siloxane (PVS) or other materials suitable for a dental impression. The scanned digital data set information is provided to a data processing system for further processing. In a distributed processing environment, the scanner may be located at a remote location and communicate scanned digital data set information to data processing system over a network interface.

Figure 3:
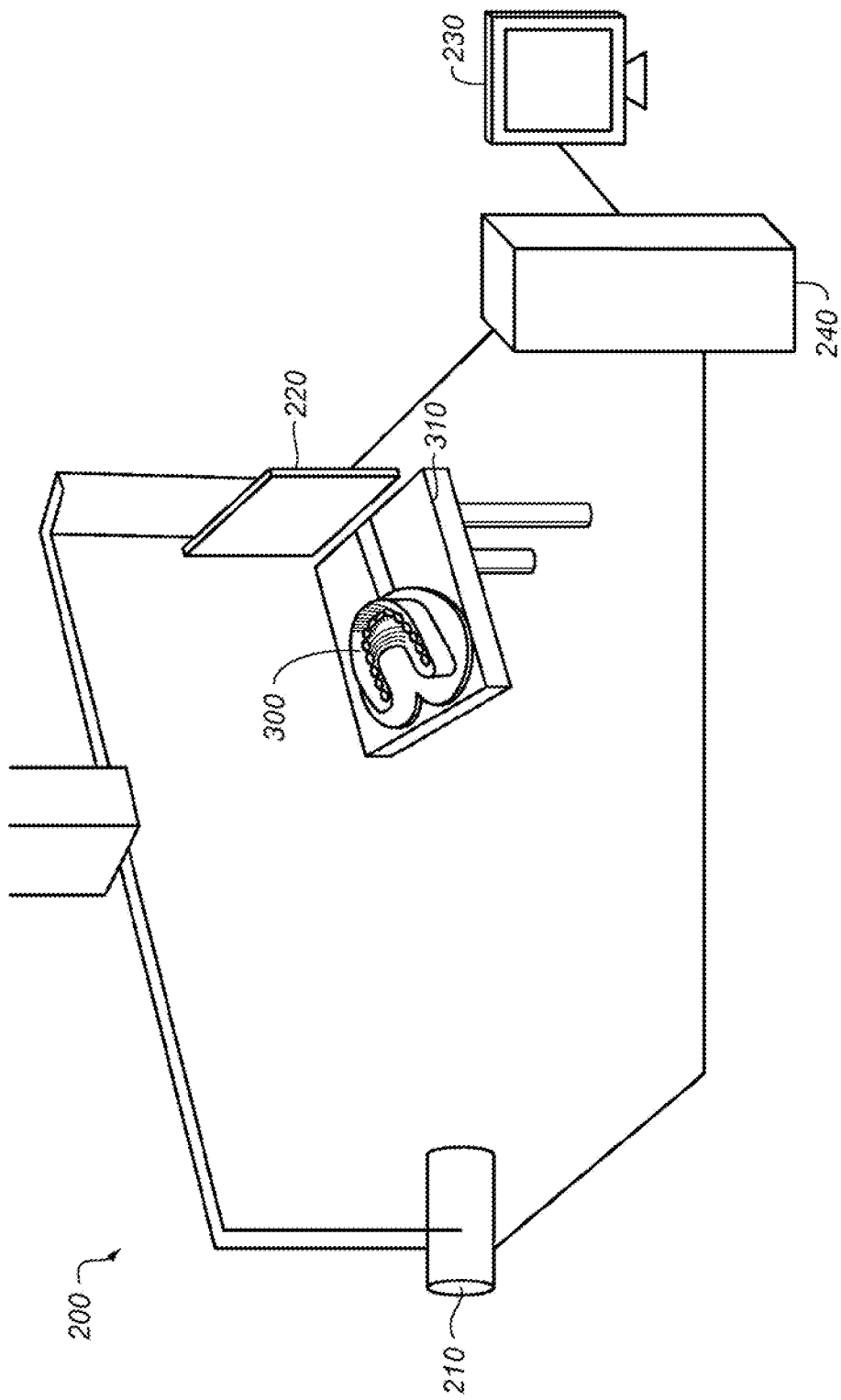
FIG. 3 shows a system for forming an image of teeth by scanning a negative impression.

Referring to FIGS. 2 and 3, an impression 300 to be scanned is placed on a table or other type of support 310. The impression 300 is irradiated by an x-ray beam emitted by x-ray source of the CT system. As is well known in the art for CT systems, radiation is swept through the impression 300 and captured for measurement by x-ray digital detector 220. The detector 220 provides the information to a computer/processor 240 for processing and displaying an image on a display 230 that is in signal communication with processor 240 and energizable to display an image. Impression 300 can be a wax bite, polyvinyl siloxane (PVS), or other type of impression material. The upper, lower, and bite impressions can be scanned using a CBCT system to generate digital scanned data. The upper and lower bite impressions can be scanned together, separately, or in various combinations.

Figure 4:
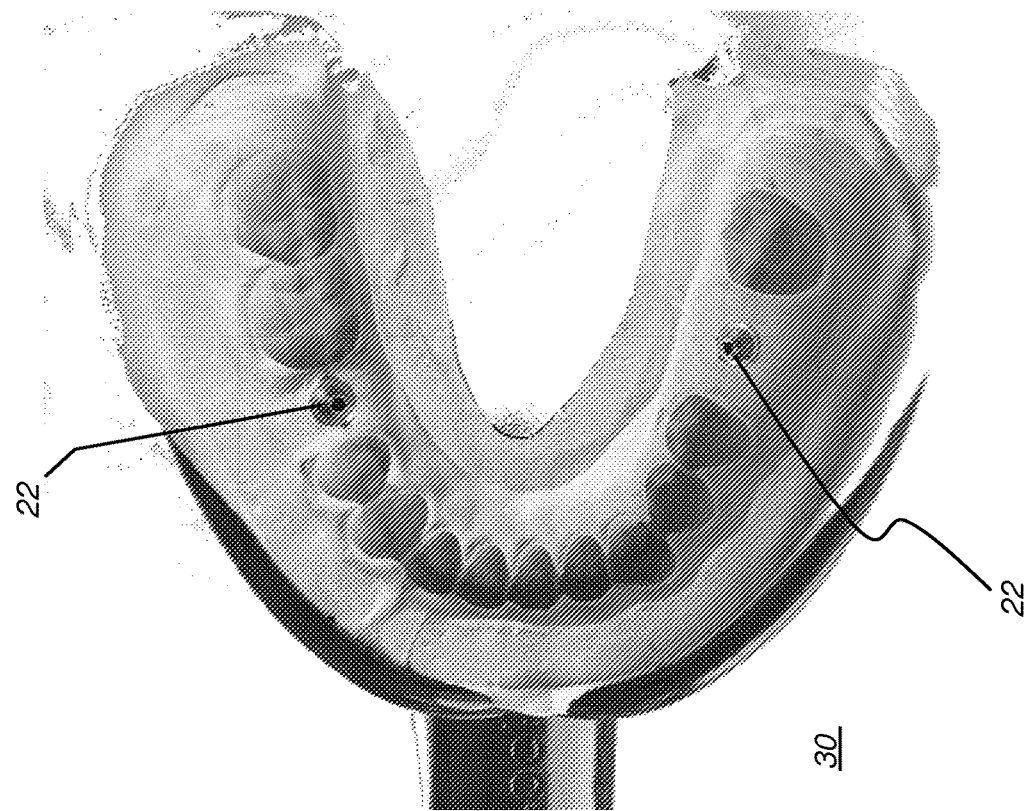
FIG. 4 shows an impression showing implant position in relation to the dentition.

In one arrangement, the negative impression of each of the upper and lower jaw are scanned as impression 300. FIG. 4 shows an exemplary impression obtained from patient dentition, with the position of implants 22 shown. In addition to the full jaw image, a wax bite (or other bite material, such as PVS) can also be scanned. The scanning of these items or of other materials used to form impression 300 can be accomplished individually or in various combinations, along with scans obtained from a stone or plaster casting of at least a portion of the upper and/or lower jaw.

Using the negative impression of the patient's teeth for the CT system's scan enables direct use of the volume data for forming a digital model and eliminates the need to create a positive dental stone or plaster model for each jaw. When using this method, software on computer 240 (FIG. 3) acquires the scan data from the impression and then automatically generates a digital positive model of the patient's teeth from the scan data of the negative impression.

The generation process employs software techniques employed for cone beam reconstruction, with processing adapted to more accurately indicate the location of teeth and related structures using information obtained from the negative impression. With this technique, a digital model of the upper and lower jaw can then be put together using the information from the scan data of a wax bite or other impression, without directing radiation to the patient and without the effort, time, and/or expense of forming a stone or plaster positive.

An exemplary embodiment of the present disclosure provides a positive digital 3D model wherein the negative impression includes one or more locator or transfer elements for implant or other prosthetic support features. In the example of FIG. 4, two implants 22 are provided as part of an impression 30. Transfer elements 20 as shown in FIG. 5A provide one type of locator element that helps the dental lab and practitioner to more accurately model the restoration and to plan its successful design and installation.

Figure 5A:
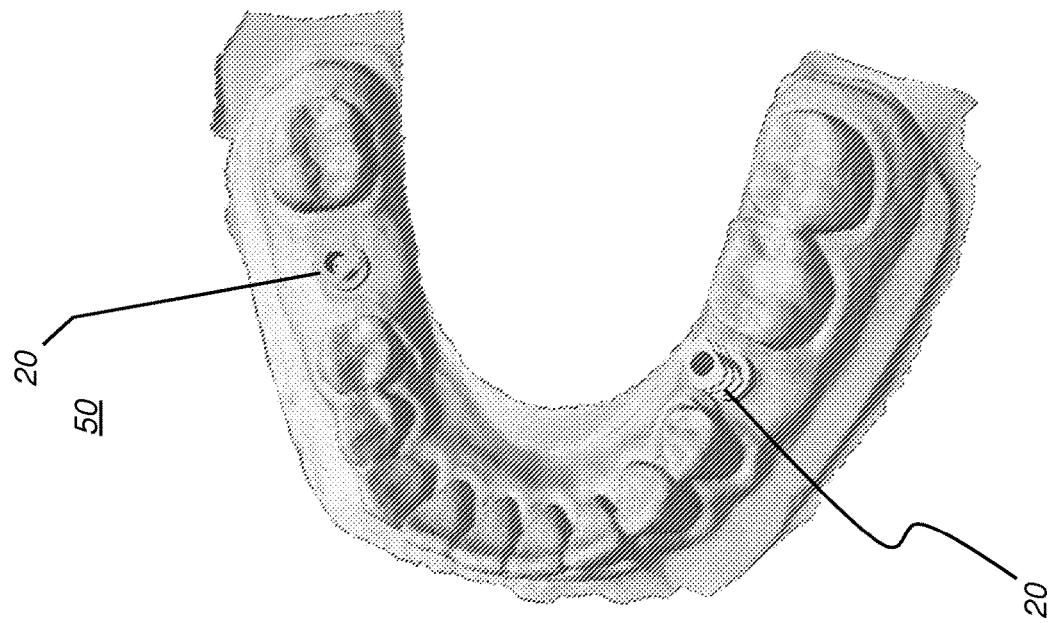
FIG. 5A shows a digital model having two implant transfer elements.

FIG. 5A shows an exemplary digital positive model 50 obtained from scanning an impression having two transfer elements 20, both shown protruding from the gum surface.

Figure 5B:
FIG. 5B shows an enlarged digital model with an implant transfer element.

FIG. 5B shows a close-up view of one transfer element 20 in a reconstructed digital positive model 50. In examples shown in FIGS. 5A and 5B, a portion of each transfer element 20 protrudes into negative impression 30; the same portion of transfer element 20 extends out from positive model 50 that is then formed from impression 30.

By forming a digital model of the patient dentition as a volume, an embodiment of the present invention allows the use of segmentation and other image analysis utilities for enhanced display and calculation using the transfer elements from a volume reconstruction.

Figure 6A:
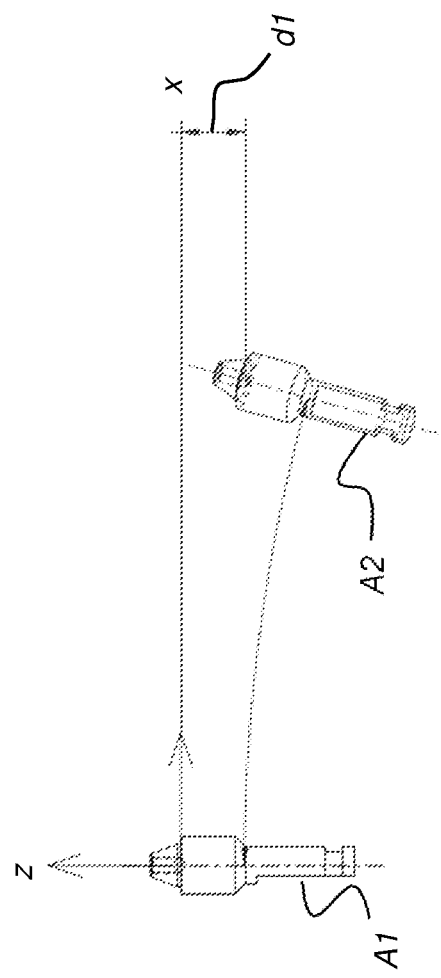
Figure 6B:
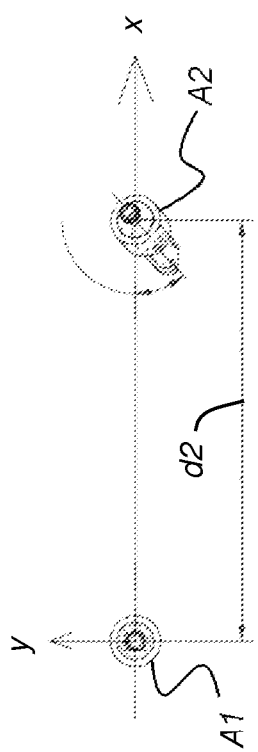

FIGS. 6A, 6B, and 6C show various geometric information that can be computed for prosthetic features such as transfer elements scanned from the impression. In the examples shown, two implant analogues A1 and A2 are shown, which can include both implant and transfer element portions, formed as one type of transfer element volume model. Similar geometry can be computed for posts or other imaged features segmented from the scan. Alternatively, selected exemplary geometries can be computed based on a scanning procedure purpose.

FIG. 6A shows analogue A1, A2 projection along an xz plane, with a relative height dimension d1. FIG. 6B shows analog A1, A2 projection relative to an xy plane, separated at a dimension d2. FIG. 6C shows analogues A1 and A2 at different projection angles and with a distance dimension d3 between top openings. Dimensions d1, d2, and d3 between transfer element models can be computed and displayed, as shown.

Figure 7:
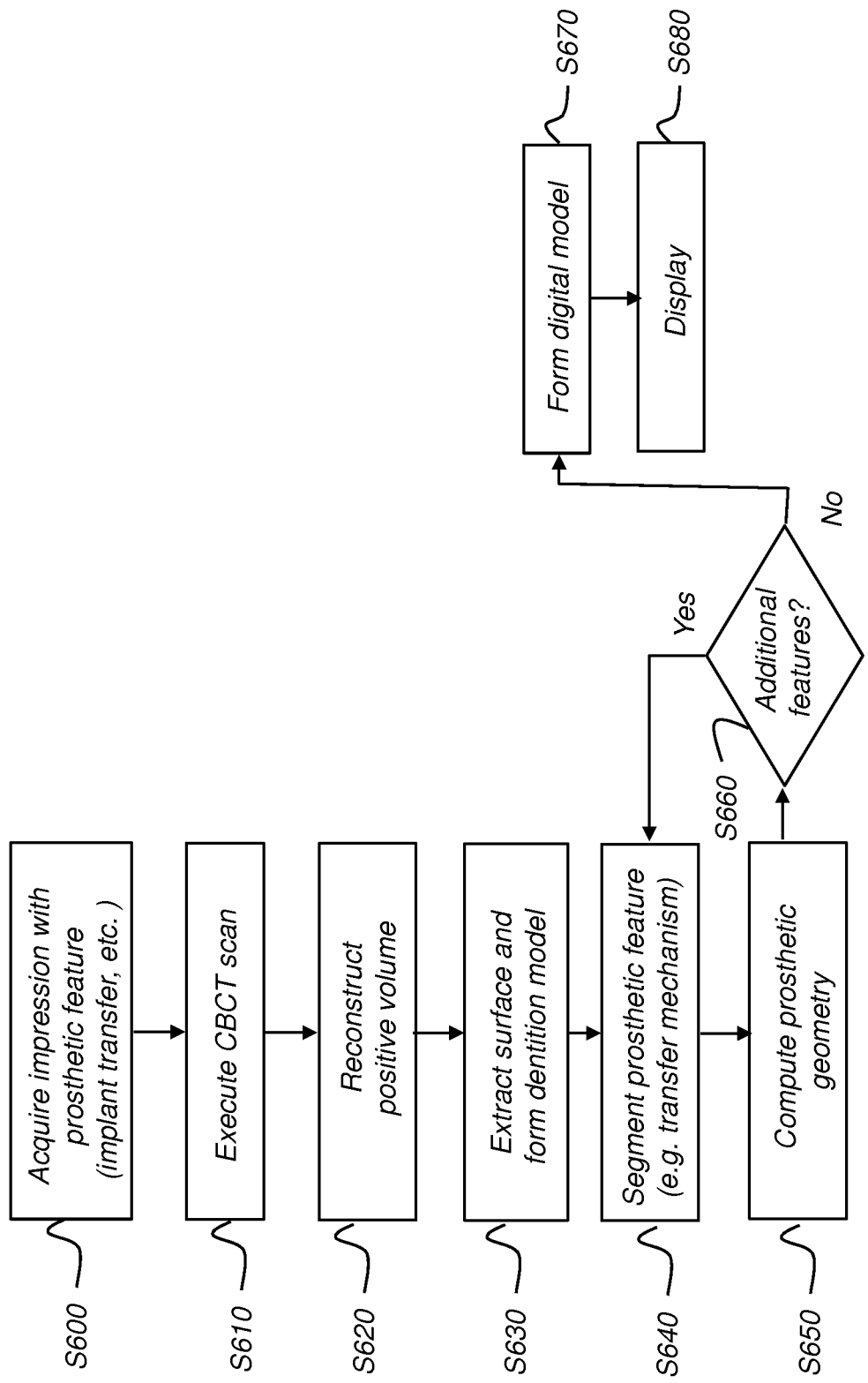
FIG. 7 is a logic flow diagram that shows an exemplary sequence embodiment for forming and displaying a digital model that shows the patient dentition and one or more transfer elements for a dental restoration.

FIG. 7 is a logic flow diagram that shows an exemplary method embodiment for forming and displaying a 3D digital model that shows the patient dentition and one or more transfer elements for a dental restoration. A preparation step S600 acquires the impression from the patient, including the transfer element. The impression is removed, the transfer element inserted, and scanned in a CBCT scanning step S610.

The transfer element can be any of several types of device, including copings that are designed to be captured by the impression material and automatically removed when the impression is pulled away from the teeth. Alternately, the transfer element can be a hardware element that remains in the mouth when the impression is removed and is geometrically keyed and designed to fit in one orientation only, in a suitably sized cavity formed in the impression. The transfer element can be a radio-opaque material, such as a titanium element for example. Having a density that is very different from the impression material allows the transfer element to be readily segmented from the impression in the obtained image volume.

The CBCT scan itself is preferably obtained at a suitable energy level for scanning the impression material. According to an embodiment, technique settings of 80 kV and 2 mA were found to provide acceptable results for scan of the impression with transfer element(s).

Continuing with the FIG. 7 sequence, a reconstruction step S620 then reconstructs the shape of the dentition that has been obtained from the impression, including the transfer element. A surface extraction step S630 extracts the surface shape of the transition between the impression and air from the scan. In this reconstructed shape, formed using exemplary scanning methods described in the Maury et al. 2016/0148370 application noted earlier, masks can be generated that define air and non-air portions of the image space. An iterative process can be used to more accurately characterize the surface as the interface of air and non-air voxels. Surface extraction provides the needed surface detail as a dentition model, an inverse of the air volume model; in reconstruction, the dentition model itself is assigned a uniform density value, based on forming an image from the air space interface or transition interface with the impression material.

The transfer element can be handled differently in reconstruction. The transfer element is actually scanned for standard CBCT reconstruction as a "positive" feature, as opposed to the "negative" reconstruction provided from the impression negative. In order to image the transfer element and clearly show its shape and position as a volume model within the scanned volume, segmentation is used. The scanned transfer element is typically a highly radio-opaque metal having attenuation characteristics that are markedly different from those of the imaged impression material. Because of the nature of this type of device, voxels are of uniform density, simplifying subsequent segmentation processing in a segmentation step S640. Segmentation step S640 forms a transfer element volume model that is positioned partially within the air volume model that bounds the impression and that is used to form the inverse model of the patient's dentition.

An optional computation step S650 then computes geometry for the transfer element and other prosthetic support elements detected in the scan. Measurements can be provided for dimensional and angular characteristics. FIGS. 6A-6C showed various exemplary geometric aspects of transfer elements from segmentation and analysis. The scanning system can display one or more calculated values related to the transfer element along at least a portion of the combined digital 3D model of the teeth. The combined digital 3D model is formed according to a bounding transition surface from the scanned negative impression and the segmentation of the transfer element, which provides information on shape and spatial position relative to the transition surface.

Continuing with the processing sequence of FIG. 7, a check step S660 determines whether segmentation and computation steps S640, S650 are completed. If not, processing returns to complete segmentation. Where segmentation and geometric processing is completed, processing continues to a digital model forming step S670, in which the 3D digital model of patient dentition is generated using the combined surface, segmentation, and geometric information from preceding steps. The transfer element volume model from segmentation step S640 is combined with the modeled patient dentition from surface extraction step S630. A display step S680 then displays the digital model to the practitioner.

Using exemplary method and/or apparatus embodiments of the present disclosure, the practitioner then has useful tools for viewing and analysis of a restoration in process, without the requirement for forming an actual stone or plaster model. Communication with the dental lab is simplified, since both the practitioner and lab can view restoration elements simultaneously. The completed reconstruction can be presented as a stereolithography (STL format) file, or data in other surface representation format, for transmission and storage.

Prior knowledge can be used to correct the volume information. For example, information about missing teeth and dimensional information can be used to validate and correct information during processing. Iterative processing for volume reconstruction may also include noise reduction processing using well-known techniques. Noise can be corrected in projection images at the pixel level, then the volume can be re-projected using adjusted projections to correct the original projection image data prior to conducting another reconstruction. This additional reconstruction with adjustment to projection images may be executed two or more times.

The generated computer model is available to the practitioner for viewing from multiple slice angles, for treatment planning, and for comparison with later imaging and with the patient's mouth as restorative treatment proceeds. In one exemplary embodiment, such procedures can be repeated for upper and lower jaws. Once the upper and lower digital models are generated, they can be aligned into a bite position using bite digital scan data or the like.

Volume reconstruction can form a volume image from the projection images using conventional techniques, such as FBP (Filtered Back-Projection) or FDK projection. With impression use, the full volume is preferably not reconstructed from projection images; only the transition surface or 3D surface mesh (e.g., tooth or dentition surface, or air-only scan data for example as described in Maury et al.) is reconstructed. Iterative processing can be performed to improve the quality of the air-only reconstruction. Surface detection techniques can be applied to determine the transition surface of the teeth and generate a transition surface that includes dentition along with visible portions of the transfer features. The transfer element or other structural feature is scanned with reference to the detected surface. A portion of the transfer element lies on each side of the reconstructed surface that has been obtained from the impression.

As is well known to those skilled in the volume image reconstruction arts, artifacts are prone to occur when there are abrupt transitions between low- and high-density materials. Abrupt difference in radio-density of materials on each side of an interface can result in data values that exceed the dynamic range of the processing electronics. This factor is of concern where the shape of the interface is of particular interest, as is the case when generating a model of the teeth. A related problem is beam hardening that occurs with polychromatic or polyenergetic radiation. Caused by the preferential attenuation of low-energy photons in a polyenergetic beam, beam hardening happens when a material that is highly dense absorbs lower energy (lower frequency) radiation so that the remainder of the beam contains higher energy. Beam hardening artifacts can vary according to the shape of the scanned object. Unless corrected, beam hardening can cause low-frequency artifacts that appear as pronounced bright and dark shadows that originate at, and extend outward from, the interface surfaces.

Classical back-projection techniques, such as conventional Feldkamp-Davis-Kress (FDK) reconstruction, assume a linear relationship between object density and object length, as described by the Beer-Lambert law, familiar to those skilled in the volume reconstruction arts. However, in practice, the Beer-Lambert law is not satisfied, due to spectral differences in absorption. Beam hardening results so that the reconstructed density of air at the vicinity of the object is reconstructed with errors and uncertainty in the delineation of the reconstructed air data envelope.

Exemplary embodiments of the present invention can correct for beam hardening and other effects using an iterative filtering technique that compensates for the polyenergetic contribution of the scan radiation, so that reconstruction uses data that more closely approximates the more accurate data that would be obtained from monochromatic radiation. With repeated iterations, beam hardening effects are successively removed so that the air volume that is generated is relatively free of artifacts.

According to exemplary method and/or apparatus embodiments, there is provided the capability to determine a digital model of a patient's teeth along with a transfer feature for a dental restoration such as an implant or crown, that can include: accessing a negative impression of the patient's teeth obtained with a post or transfer element in place; using a CBCT system, scanning the impression of the patient's teeth with an inserted transfer element to generate scan data; and automatically generating a positive digital model of a portion of the patient's teeth using the generated scan data, the generating being accomplished without digitally reversing the scan data. There is further provided an exemplary method embodiment to create a digital model of a patient's teeth and transfer features, including accessing a negative impression of the patient's teeth; using a CBCT system, scanning the impression of the patient's teeth to generate scan data; and automatically generating a positive digital model of a portion of the patient's teeth using the generated scan data, the generating being accomplished without digitally reversing the scan data. This method can be executed with an impression creating using a tray.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as host processor 240 as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can provide a digital model of a patient's teeth, using an impression of the patient's teeth and scanning the impression using an X-ray source to generate the digital model, where the model can also show position and orientation of features used for implant, crown, orthodontic, and/or other treatments. Exemplary embodiments according to the application can include various features described herein (individually or in combination). Although embodiments of the present disclosure are illustrated using dental imaging apparatus, similar principles can be applied for other types of diagnostic imaging and for other anatomy.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A method comprising the steps of:
obtaining a plurality of projection images acquired by scanning a negative impression of the patient's teeth using a computed tomographic imaging apparatus, wherein the impression includes a radio-opaque transfer element for a dental implant or crown post;
forming a reconstructed volume from the plurality of projection images;
defining an air volume model within the reconstructed volume and bounded by a transition surface defined according to the negative impression;
defining a transfer element volume model of the radio-opaque transfer element, segmented from the air volume model and from the transition surface;
forming a combined digital 3D model of the patient's teeth according to the air volume model and transfer element volume model; and
displaying at least a portion of the combined digital 3D model of the teeth.

2. The method of claim 1 wherein the step of obtaining the plurality of projection images comprises obtaining images from a cone-beam computed tomography apparatus.

3. The method of claim 1 further comprising a step of refining the air volume model by forming a binary mask volume representative of the air volume and of the negative impression.

4. The method of claim 1 further comprising a step of assigning a uniform density to voxels of the air volume model.

5. The method of claim 1 wherein the combined digital 3D model is represented as a file in STL format.

6. The method of claim 1 wherein the impression is formed from polyvinyl siloxane.

7. The method of claim 1 wherein the radio-opaque transfer element is formed from titanium.

8. A method comprising the steps of:
obtaining a plurality of projection images acquired by scanning a negative impression of the patient's teeth using a computed tomographic imaging apparatus, wherein the impression includes a radio-opaque transfer element for a dental implant or crown post;
forming a reconstructed volume from the plurality of projection images;
defining an air volume model within the reconstructed volume and forming a dentition model bounded by a transition surface defined according to the negative impression;
defining a transfer element volume model of the radio-opaque transfer element, segmented from the air volume model and from the transition surface;
forming a combined digital 3D model of the patient's teeth according to the dentition model and transfer element volume model, wherein a portion of the transfer element volume model extends outward from a surface of the dentition model;
displaying one or more calculated values related to the radio-opaque transfer element along at least a portion of the combined digital 3D model of the teeth; and
displaying at least a portion of the combined digital 3D model of the teeth.

9. The method of claim 8 wherein the combined digital 3D model is represented as a data file in a surface representation format.

10. The method of claim 8 wherein the transfer element volume model includes both transfer element and implant portions.

11. A method comprising the steps of:
obtaining a plurality of projection images acquired by scanning a negative impression of the patient's teeth using a computed tomographic imaging apparatus, wherein the impression includes a radio-opaque transfer element for a dental implant or crown post;
forming a reconstructed volume from the plurality of projection images;
defining an air volume model within the reconstructed volume and bounded by a transition surface defined according to the negative impression;
defining a transfer element volume model of the radio-opaque transfer element, segmented from the air volume model and from the transition surface; and
forming a combined digital 3D model of the patient's teeth according to the air volume model and transfer element volume model.

12. The method of claim 11 wherein the step of obtaining the plurality of projection images comprises obtaining images from a cone-beam computed tomography apparatus.

13. The method of claim 11 further comprising a step of refining the air volume model by forming a binary mask volume representative of the air volume and of the negative impression.

14. The method of claim 11 further comprising a step of assigning a uniform density to voxels of the air volume model.

15. The method of claim 11 wherein the combined digital 3D model is represented as a file in STL format.

16. The method of claim 11 wherein the impression is formed from polyvinyl siloxane.

17. The method of claim 11 wherein the transfer element is formed from titanium.

18. A method comprising the steps of:
obtaining a plurality of projection images acquired by scanning a negative impression of the patient's teeth using a computed tomographic imaging apparatus, wherein the impression includes a radio-opaque transfer element for a dental implant or crown post;
forming a reconstructed volume from the plurality of projection images;
defining an air volume model within the reconstructed volume and forming a dentition model bounded by a transition surface defined according to the negative impression;
defining a transfer element volume model of the radio-opaque transfer element, segmented from the air volume model and from the transition surface;
forming a combined digital 3D model of the patient's teeth according to the dentition model and transfer element volume model, wherein a portion of the transfer element volume model extends outward from a surface of the dentition model; and displaying one or more calculated values related to the radio-opaque transfer element along at least a portion of the combined digital 3D model of the teeth.

19. The method of claim 8 wherein the combined digital 3D model is represented as a data file in a surface representation format.

20. The method of claim 8 wherein the transfer element volume model includes both transfer element and implant portions.

* * * * *